US006193654B1

United States Patent
Richardson et al.

(10) Patent No.: US 6,193,654 B1
(45) Date of Patent: Feb. 27, 2001

(54) COMPUTERIZED METHOD AND SYSTEM FOR MEASURING AND DETERMINING NEONATAL SEVERITY OF ILLNESS AND MORTALITY RISK

(75) Inventors: Douglas K. Richardson, Newton, MA (US); Gabriel J. Escobar, Lafayette, CA (US); Shoo Lee, Vancouver (CA)

(73) Assignee: Beth Israel Deaconess Medical Center, Boston, MA (US)

( * ) Notice: Subject to any disclaimer, the term of this patent is extended or adjusted under 35 U.S.C. 154(b) by 0 days.

(21) Appl. No.: 09/195,892

(22) Filed: Nov. 19, 1998

Related U.S. Application Data

(60) Provisional application No. 60/066,899, filed on Nov. 20, 1997.

(51) Int. Cl.[7] ............................................. A61B 5/00
(52) U.S. Cl. .......................... 600/300; 600/301; 600/481
(58) Field of Search ................................... 600/300–301, 600/481–486, 500–504, 529–534, 538; 128/900–925, 897–898; 705/2–3, 5–9

(56) References Cited

U.S. PATENT DOCUMENTS

| | | | |
|---|---|---|---|
| 5,639,617 | * | 6/1997 | Bohuon ................................ 600/300 |
| 5,809,477 | * | 9/1998 | Pollack ................................... 705/2 |
| 5,835,897 | * | 11/1998 | Dang ...................................... 705/2 |
| 5,857,966 | * | 1/1999 | Clawson ................................. 705/3 |
| 5,989,187 | * | 11/1999 | Clawson ................................. 705/3 |

FOREIGN PATENT DOCUMENTS 0 764 914 A2    3/1997 (EP) .

OTHER PUBLICATIONS

Pollack, M.M. et al., "Prism III: An Updated Pediatric Risk of Mortality Score," *Critical Care Medicine* 24:5, pp. 743–752 (1996).

Pollack, M.M. et al., "The pediatrick risk of mortality III—Acute physiology score (PRISM III–APS) : A method of assessing physiologic instability for pediatric intensive care unit patients," *Journal of Pediatrics* 131:4, pp. 575–571 (Oct. 1997).

(List continued on next page.)

*Primary Examiner*—Cary O'Connor
(74) *Attorney, Agent, or Firm*—Hamilton, Brook, Smith & Reynolds, P.C.

(57) ABSTRACT

A computerized method and system for measuring and determining severity of illness of a neonatal ICU patient uses a computer and a software program to process measured parameter values from preselected physical conditions. Measurement ranges for each measured physical condition are divided into contiguous zones; the contiguous zones are given predetermined weighting factors using the software program. The software program, using user inputs, optimally selects a single value of each measured physical condition from several measurements. The single selected value of each parameter is then modified using the software program. In one embodiment, for achieving the modification, the software program provides a predetermined weighting factor depending on the parameter value selection. For each selected measured value, an applicable zone and its predetermined weighting factor is determined to generate a modified partial score representing each measured physical condition. Values of modified partial scores for all the measured physical conditions are summed by the computer using the software program to provide an illness-severity measure which can be compared with data held in a database for similar patient population. As described in one embodiment, the physical conditions preselected are: lowest mean blood pressure, lowest pH, lowest temperature, lowest oxygenation ratio, urine output, and the presence of multiple seizures. Three additional measurements of birth weight, smallness for gestational age and low Apgar score, after optimal selection and modification as provided by the program, are used to provide a mortality rate assessment for a neonatal patient being monitored.

30 Claims, 4 Drawing Sheets

OTHER PUBLICATIONS

LeGall, J., "A New Simplified Acute Physiology Score (SAPS II) Based on a European/North American Multicenter Study," *JAMA 270:24*, pp. 2957–2963 (Dec. 1993).

The International Neonatal Network, "The CRIB (clinical risk index for babies) Score: A Tool for Assessing Initial Risk and Comparing Performance of Neonatal Intensive Care Units", *The Lancet*, vol. 342: p. 193–8; Jul. 24, 1993.

R.F. Maier, et al., "Comparison of Mortality Risk: A score for Very Low Birthweight Infants", *Archives of Disease in Childhood*, vol. 76: p. F146–F151; 1997.

Pollack, Murray M., et al., "Pediatric Risk of Mortality (PRISM) Score", *Critical Care Medicine*, 1998: 16:1110–1116.

Knaus, W.A. et al., "APACHE–Acute Physiology and Chronic Health Evaluation: a Physiologically–Based Classification System", *Critical Care Medicine*; 1981; 9:591–597.

Knaus, W.A., et al., "APACHE II: A Severity of Disease Classification System", *Critial Care Medicine*; 1985; 13:818–829.

Richardson, D.K., et al., "Neonatal Risk Scoring System", *Clinics in Perinatology*; 1998; 25:591–611.

Richardson, D.K., et al., "Measuring Illness Severity in Newborn Intensive Care", *J Intensive Care Med*; 1994; 9:20–23.

Richardson, D.K., et al., "Birth Weight and Illness Severity: Independent Predictors of Neonatal Mortality", *Pediatrics*; May 1993; 91:969–975.

Richardson, D.K., et al., "Score for Neonatal Acute Physiology: A Physiologic Severity Index for Neonatal Intensive Care", *Pediatrics*; Mar. 1993; 9:1–7.

Gray, J. E., et al, "Neonatal Therapeutic Intervention Scoring System: A Therapy–Based Severity–of–Illness Index", *Pediatrics*; Oct. 1992; 90:561–567.

Seligmann, J. and Sulavik, C, "Software for Hard Issues: Who Will Live? Who Will Die? A Computer Votes", *Newsweek*; Apr. 27, 1992; p. 55.

Wong D.T. and Knaus, W.A., Predicting Outcome in Critical Care: The Current Status of the APACHE Prognostic Scoring System, *Can J Anaesth*; 1991; 38:374–383.

Knaus, W.A. et al., "The APACHE III Prognostic System:Risk Prediction of Hospital Mortality for Critically Ill Hospitalized Adults" *Chest*; 1991; 100:1619–1636.

Pollack; M.M. et al, "Accurate Prediction of the Outcome of Pediatric Itensive Care", *N.E. Journal of Medicine*; Jan. 15, 1987; 316:134–139.

Wagner, D.P., et al., "Physiologic Abnormalities and Outcome from Acute Diseases", *Arch Intern Med*; 1986; 146:1389–1396.

Knaus, W.A., et al., "Relationship Between Acute Physiologic Derangement and Risk of Death", *J Chron Dis*; 1985; 38:295–300.

Yeh, T.S., et al., "Validation of Physiologic Stability Index for Use in Critically Ill Infants and Children", *Pediatric Research*; 1984; 18:444–451.

LeGall, J–R, et al., "A Simplified Acute Physiology Score for ICU Patients", *Critical Care Medicine*; 1984; 12:975–977.

Wagner, D.P., et al., "Statistical Validation of a Severity of Illness Measure", *American Journal of Public Health*; 1983; 73:878–884.

Keene, A.R. and Cullen, D.J., "Therapeutic intervention Scoring System:Update 1983", *Critical Care Medicine*; 1983; 11:1–3.

Cullen, D.J. et al., "Therapeutic Intervention Scoring System:A method for Quantitative Comparison of Patient Care", *Critical Care Medicine*; 1974; 2:57–60.

* cited by examiner

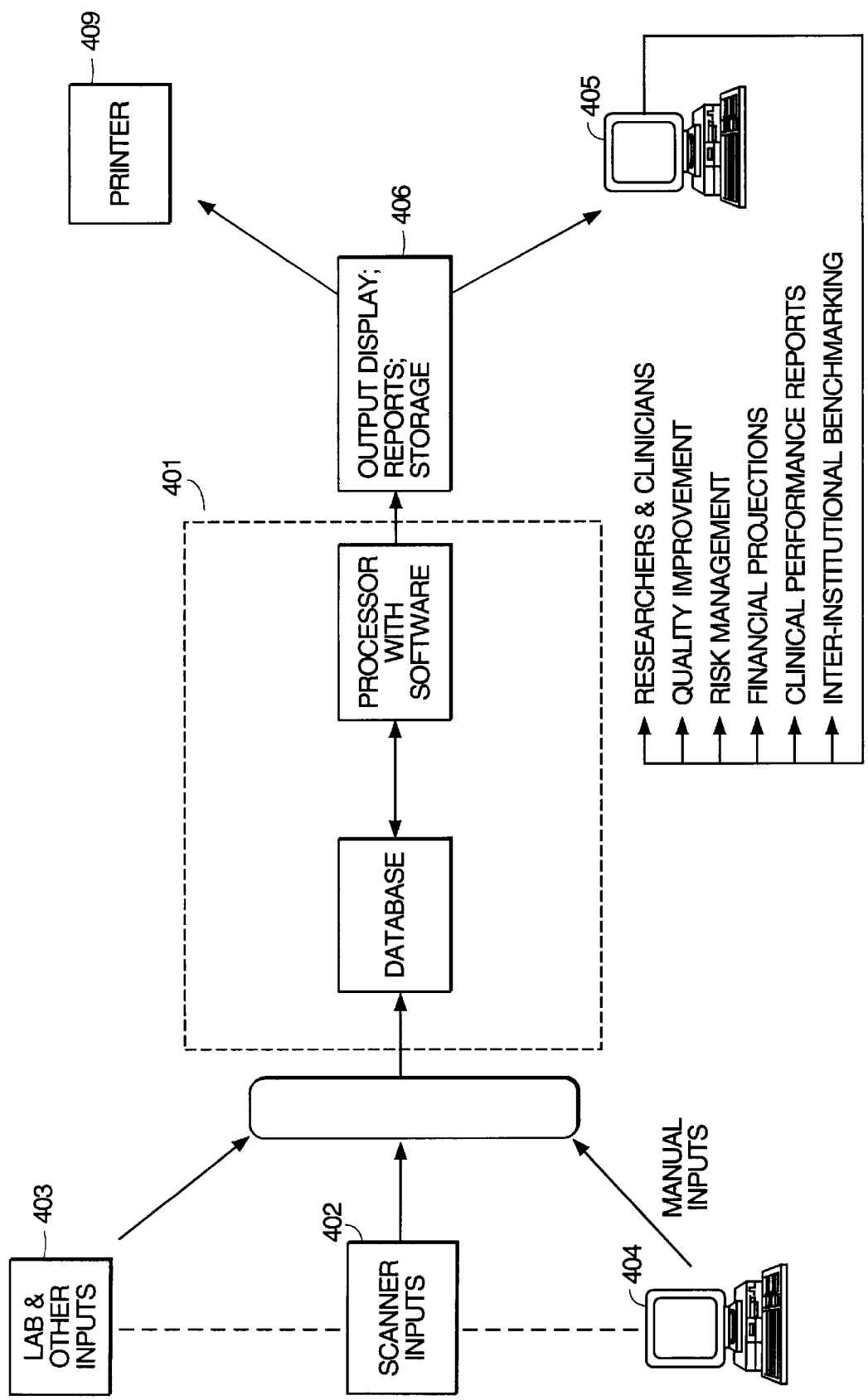

COMPUTERIZED METHOD AND SYSTEM FOR MEASURING AND DETERMINING NEONATAL SEVERITY OF ILLNESS AND MORTALITY RISK

FIELD OF THE INVENTION

This application claims the benefit of U.S. provisional application serial No. 60/066,899, filed Nov. 20, 1997, the contents of which are incorporated herein by reference.

This invention relates to an improved method and system for determination of illness severity of patients particularly in newborn/neonatal intensive care units (ICUs). The invention also provides a method and system for determining the mortality risk of neonatal ICU patients as an extension of a determined illness severity. Applicants are endeavoring to publicize the system of the present invention to be known as SNAP-II, which stands for Score for Neonatal Acute Physiology II, a successor for a system earlier know as SNAP, which stands for Score for Neonatal Acute Physiology.

BACKGROUNDS OF THE INVENTION

Monitoring and treatment of premature infants or critically ill newborns is complicated and expensive. The efficacy of the monitoring system, among other things, depends on which parameters are being monitored, and how many of the measurements can be made automatic without human intervention, without sacrificing system reliability.

Several approaches to measurement of illness severity have been known to be used hitherto, and those have varying degrees of cost and reliability. Most known approaches have been devised, however, without specific emphasis on the patient to be monitored being a neonatal intensive care unit (NICU) patient.

DESCRIPTION OF PRIOR ART

Nearly all IC (intensive care) illness severity scores based on physiologic derangements have been directly or indirectly derived from the Acute Physiology and Chronic Health Evaluation (APACHE) score by Knaus et al. (see Knaus et al. "APACHE—acute physiologically based classification system" Crit Care Med, 1981;9(8):51–597). He reasoned that derangements from physiologic norm are a measure of illness, and the more severe the derangements, the more severe the illness. He selected and weighted 34 vital signs and laboratory results routinely available in the first 24 hours of admission to form the APACHE. He showed that higher scores correlated with death, morbidity, and resource use (see Knaus et al. "APACHE—acute physiologically based classification system" Crit Care Med, 1981;9(8):591–597). The advantage generally of such physiology-based measures is that they are objective, reliable, and credible. APACHE was simplified to APACHE-II (see Knaus et al. "APACHE II: A severity of disease classification system" Crit Care Med, 1985; 13(10):818–829), and was copied and simplified into the Simplified Acute Physiology Score (SAPS) (see Le Gall et al. "A simplified acute physiology score for ICU patients" Crit Care Med, 1984;12:975–7). With increasing sophistication, each of these was revised into APACHE-III (see Knaus et al. "The APACHE III prognostic system. Risk prediction of hospital mortality for critically ill hospitalized adults" Chest 1991;100:1619–36) and SAPS-II respectively (see Le Gall et al. "A new simplified Acute Physiology Score {SAPS II} based on a European/North American multicenter study" JAMA 1993;270:2957–63).

In pediatric intensive care, APACHE was modified to create the Physiologic Stability Index (PSI)(see Yeh et al. "Validation of a physiologic stability index for use in critically ill infants and children" Pediatr Res 1984; 18:445–451), which was then simplified to create the Pediatric Risk of Mortality Score (PRISM) (see Pollack et al. "Pediatric Risk of Mortality {PRISM} score" Crit Care Med, 1988; 16:1110–1116), and later the PRISM-III (see Pollack et al. "PRISM III: an updated Pediatric Risk of Mortality score" Crit Care Med, 1996; 24:743–52) and PRISM-III APS (for "Acute Physiology Score") (see Pollack et al. "The Pediatric Risk of Mortality III—Acute Physiology Score {PRISM III-APS}: a method of assessing physiologic instability for pediatric intensive care unit patients" J Pediatr 19971 131:575–81).

Prior Art: Illness Severity Scores for Newborns

The importance of measuring illness severity became clear in neonatal intensive care which prompted similar score development. In 1993, Richardson, et al. used the APACHE concepts but all new variables in creating and validating the Score for Neonatal Acute Physiology (SNAP) (see Richardson et al. "Score for Neonatal Acute Physiology {SNAP}: Validation of a new physiology-based severity of illness index" Pediatrics 1993; 91:617–623). William Tarnow-Mordi, et al. used the PRISM concept and all new variables in creating and validating the Clinical Risk Index for Babies (CRIB) in 1993 (see International Neonatal Network "The CRIB {clinical risk index for babies score}—a tool for assessing initial neonatal risks and comparing performance of neonatal intensive care units" Lancet 1993; 342:193–198). SNAP is a 34-item physiology-based score measuring severity of illness, applicable to all newborn intensive care unit (NICU) admissions.

Based on the same concepts published for APACHE and PRISM, Dr. William Tarnow-Mordi derived and validated the CRIB (Lancet 1993:342;193–198) for very low birth weight infants (<1500 grams) treated in NICUs in Great Britain. CRIB uses only three physiologic variables, derived from routine vital signs and laboratory values, along with three standard markers for newborn risk, i.e., birth weight, gestational age and the presence of a life-threatening congenital anomaly. CRIB is in widespread use for research in Europe. There are, however, several important shortcomings of CRIB:

a. Validated only for very premature infants (<1500 gm): While this is valuable for research purposes, it is unacceptably restrictive for hospital and ICU managers who need to assess performance of all admissions, not just a special subset. The present invention, in contrast, is validated for all birth weights.

b. Questionable performance for outborn babies: The CRIB makes assumptions about incomplete records that are untenable for infants under emergency transport conditions. The present invention begins scoring only after the infant enters the ICU, thereby avoiding measurement assumptions.

c. Admission-only score, no sequential scoring: CRIB is designed to reflect severity only in the first day of life. Half of its components are fixed at birth (birth weight, gestational age, presence of anomalies). The present invention has a much broader dynamic range, designed to measure changing condition over time. All of the adult and pediatric scoring systems have this broader dynamic range characteristic.

d. Single organ-system: CRIB's physiologic items sample only the respiratory system. This may be adequate in a homogeneous population of very premature infants all of whom will have degrees of respiratory failure as their illness on admission. For full term infants, a much wider variety of organ-system failures requires a broader sample of organ-system items. The present invention samples several organ systems.

The "Berlin" score is a recently reported German score (Maier RF, Arch Dis Child 1997; 76:F146–F151) and is more of an epidemiologic adjustment tool than a true neonatal illness severity score. It too is an admission-only score and applies only to very premature babies (<1500 grams).

There are several other important adult ICU scores that require mention, because they have used parallel techniques to construct the scoring systems.

Mortality Prediction Model (MPM): A series of mathematically sophisticated adult ICU risk order was developed by Teres and Lemeshow (Care Med 1987; 15:208–213). A brief attempt at commercializing these appeared to be unsuccessful.

SAPS I and SAPS II: The unwieldiness of the original APACHE led to an independent revision by LeGall et al. (Le Gall JR: Crit Care Med 1984; 12:975–7) into the Simplified Acute Physiology Score (SAPS), creating a direct competitor to the concurrently derived APACHE II. Later, with the collaboration of the inventors of the MPM, the SAPS inventors revised and simplified their score to create SAPS II (LeGall JR: JAMA 1993; 270:2957–63). The SAPS has been developed in France and used widely throughout Europe.

A need still exists in healthcare to provide a system and method which obviates the shortcomings and disadvantages of known systems and methodology for determining severity of illness of patients, in particular, neonatal ICU patients from the moment of admission.

SUMMARY OF THE INVENTION

It is an object of the invention to provide a computerized method and system for determining severity of illness of a neonatal patient, using a computer method and process, and other measurement hardware. The invention, in its broad form, resides in a computerized method of making an on-line determination of illness-severity of a neonatal patient in a predetermined time span, by using a software program and optimal weighted measurement values of a predetermined 'n' number of on-line parameters from the patient being monitored, said parameters relating to n measurable predetermined physical conditions, said method comprising the steps of:

(a) obtaining, in said predetermined time span from the neonatal patient being monitored, several carefully selected values of each of said n physical conditions and producing, using a program, a single optimal value from said plurality of measured values for each of n measured physical conditions;

(b) using said software program, obtaining from said single optimal value a modified weighting partial score, thus generating n modified weighted partial scores for n on-line parameters from the patient being monitored; and (c) summing the n modified weighted partial scores to provide an indication of illness-severity of the neonatal patient, which severity indication can be displayed and compared with other known values from databases.

It is another object of the invention to provide a computerized method and system for measuring a mortality risk level of a neonatal ICU patient from the measure of illness severity.

Applicants have reviewed the measurement of illness severity in newborns and concluded that no comparable scale development has occurred in neonatal intensive care until now. To a large degree, birth weight has successfully served as a proxy indicator for severity of illness along with other risk factors including gestational age, sex and race. Nonetheless there is strong evidence as presented above that these prior art models fail to accurately capture severity of illness as evidenced by the large residual variation in studies of mortality and newborn lung disease.

Used in applicants' invention is a selection of scale items, and scoring of therapies and physiologic derangements. Applicants followed the APACHE convention of abstracting the most severely deranged physiology in a 24-hour period following admission. The hypothesis to be tested was that the traditional risk factors (including birth weight, Apgars, sex, race, etc.) were strong predictors of mortality across the birth weight spectrum, but inadequate for distinguishing mortality risks within birth weight strata.

A comparison of variations in outcomes and resources is one application/use of the present invention. Another use is the refinement and improvement of the prior study. In as much as SNAP-II is a scoring system to classify illness severity in newborns in intensive care units (NICUs), it measures the degree of physiologic derangement across multiple organ systems, using vital signs and laboratory values and other information routinely recorded in clinical records. Five core components of the present system, which are significant, are:

1. Score items: Of the hundreds of potential markers of newborn illness severity, Applicants have selected a very limited subset that are reliably available, easily captured, and robust as predictors. This specific list of variables, and their exact definitions, are unique to the present invention improvement over SNAP.

2. Items score weights: Each score item is weighted according to a carefully derived risk value, so that less serious items have relatively low score points, and more serious items have relatively high score points. The SNAP-II is the sum of points for each item. These variables and weights have been derived on an initial large cohort of patients, and then validated on a second large cohort. The present invention improvement takes into account two subscores.
   a. Risk factors: These are standard, scientifically recognized risks for neonatal mortality, including birth weight, gestational age, Apgar scores and gender.
   b. Acute Physiology Score: These items reflect the severity of physiologic derangement.

3. Equations and coefficients: These equations associate the SNAP-II (or its individual components) with an array of outcomes, resource use, costs and process benchmarks. They are derived from regression equations (linear, logistic, polynomial) through a model fitting process that involves modification of the input variables and selective inclusion to optimize the discrimination and calibration of the equations.

4. Reference database: This database consists initially of the combined NICU data sets from the 7 NICU research study in New England, funded by AHCPR, and the six NICU study in California, funded by Kaiser Permanente Division of Research, and the 18 NICU data set of the Canadian NICU network, founded by the Canadian Medical research council.

5. Reporting systems: These reports lay out risk-adjusted comparisons of pre-specified groups of patients in an individual NICU with an appropriate reference group, drawn from the reference database.

The present invention improvement is unique compared to other newborn severity scores in several ways: it is shorter and simpler to use than the original SNAP. It applies to all newborns admitted to NICUs, in contrast to the CRIB score which applies only to babies weighing <1500 grams. It is adaptable to sequential scoring, so that new scores can be generated daily. In contrast, CRIB is an admission-only score. The present invention is distinct from the adult and pediatric illness severity scores of prior art in that it applies specifically to newborns in NICUs. The APACHE I, II, and III, and SAPS I and II are not applicable to newborns. The PRISM, PRISM II, and PRISM III APS were derived using some full term newborns but their applicability and calibration specifically for premature infants has never been evaluated. Thus, even though in prior art, several attempts have been made to provide systems which are intended to provide an indication of the illness severity of a patient, there have been the following significant disadvantages in applying them to neonatal care situations:

in some prior art systems, as many as 34 different physical condition measurements were used, thus making the process very elaborate, expensive, and prone to miscalculation;

efforts to reduce the number 34 were made, but an identification of those physical conditions/parameters which would be crucial to neonatal situations was not made based on available illness severity scores from similar patient population;

A concerted effort was apparently not made in prior art to make an automated selection and optimization from several available readings or measured values of a single physical condition for neonatal applications over a predetermined time span.

The choice of the single optimized selected measured value of a given physical condition/parameter in the present invention is so made by a program that the choice is linked with the most appropriate weighting factor based on vast amounts of accumulated prior data, and the choice additionally ensures the highest possible reliability of the severity measurements generated. Certain physical conditions selected for being monitored in prior art were not ideally the best suitable physical conditions for neonatal measurements.

For instance, in the present invention, in a preferred embodiment, the physical conditions chosen for monitoring are blood pressure, temperature, oxygenation ratio, serum pH, presence/absence of seizures and urine output. The program in one preferred embodiment makes the optimal choice of those parameters as the lowest mean blood pressure, the lowest temperature, lowest oxygenation ratio, the lowest serum pH, presence/absence of seizures, and urine output. Consequently, in at least three of the six physical conditions selected for neonatal monitoring, four of the physical conditions offer optimal selection by the program resulting in the choice of the lowest of measurements. The fact that the lowest of the measurements for blood pressure, temperature, oxygenation ratio and serum pH were selected by the program is also associated with certain predetermined weighting factors which would result in the most reliable illness severity determination when compared with available data of similar patient population.

Alternatively, if instead of the lowest measured values of blood pressure, temperature, oxygenation ratio, and serum pH, other values were to be chosen by the program, the weighted factors to be used would correspondingly be different, in order to ensure reliability of the resulting illness severity measurement.

Applicants have found the use of the lowest mean blood pressure, lowest serum pH, lowest temperature, lowest oxygen ($pAO_2/FiO_2$) ratio, as well as urine output and the presence of multiple seizures, along with the weighted factors disclosed herein would provide an extremely highly reliable measurement of the illness severity for neonatal patients.

The task of selecting a single optimal measurement value from several generated measurement values of a physical condition, and the task of matching up the selected optimal measurement based on the nature of the optimization, for e.g., the selection having to be the lowest value with an appropriate weighting factor, is done by a computer program in the present invention.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 4 illustrates an alternative embodiment for the inventive system illustrating a processor including the monitoring software and its interaction with inputs and outputs as shown,

DETAILED DESCRIPTION OF PREFERRED EMBODIMENTS

Figure 1:
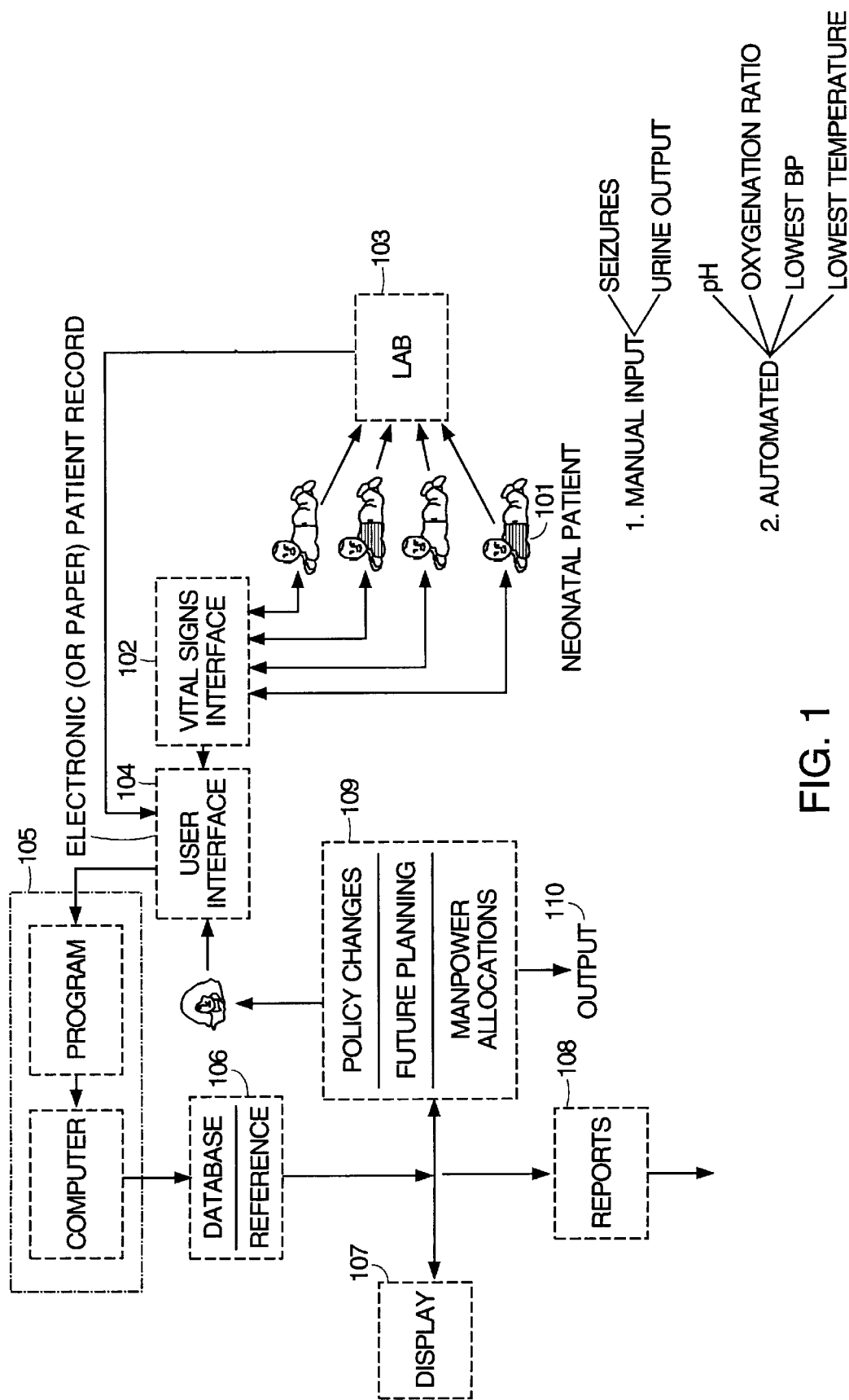
FIG. 1 is a schematic system diagram of a preferred embodiment of the invention illustrating neonatal patients being monitored and with a vital signs interface, programmed computer, database, and a laboratory interacting.

FIG. 1 illustrates components of the system of an embodiment of the invention, wherein neonatal patients admitted to the NICU 101 are monitored to obtain measurements of standard vital signs and/or other predetermined parameters such as, for example, blood pressure, temperature measurements, urine output, and presence or absence of multiple seizures. These individual values are collected 102 and registered on the computerized (or paper) patient records. Laboratory results on individual patients are similarly registered on patient records.

At fixed time intervals, all readings of the six key physiological parameters are obtained and transmitted to the computational software 105 as necessary. A measured parameter may have several recorded values in the specified time interval. The worst value, for example, is selected using carefully defined predetermined criteria. The degree of derangement is ascertained and a partial score is assigned for each parameter. In the illustrated embodiment, the weighting consists of multiplying each worst parameter with a predetermined score for the measured parameter.

Figure 3:
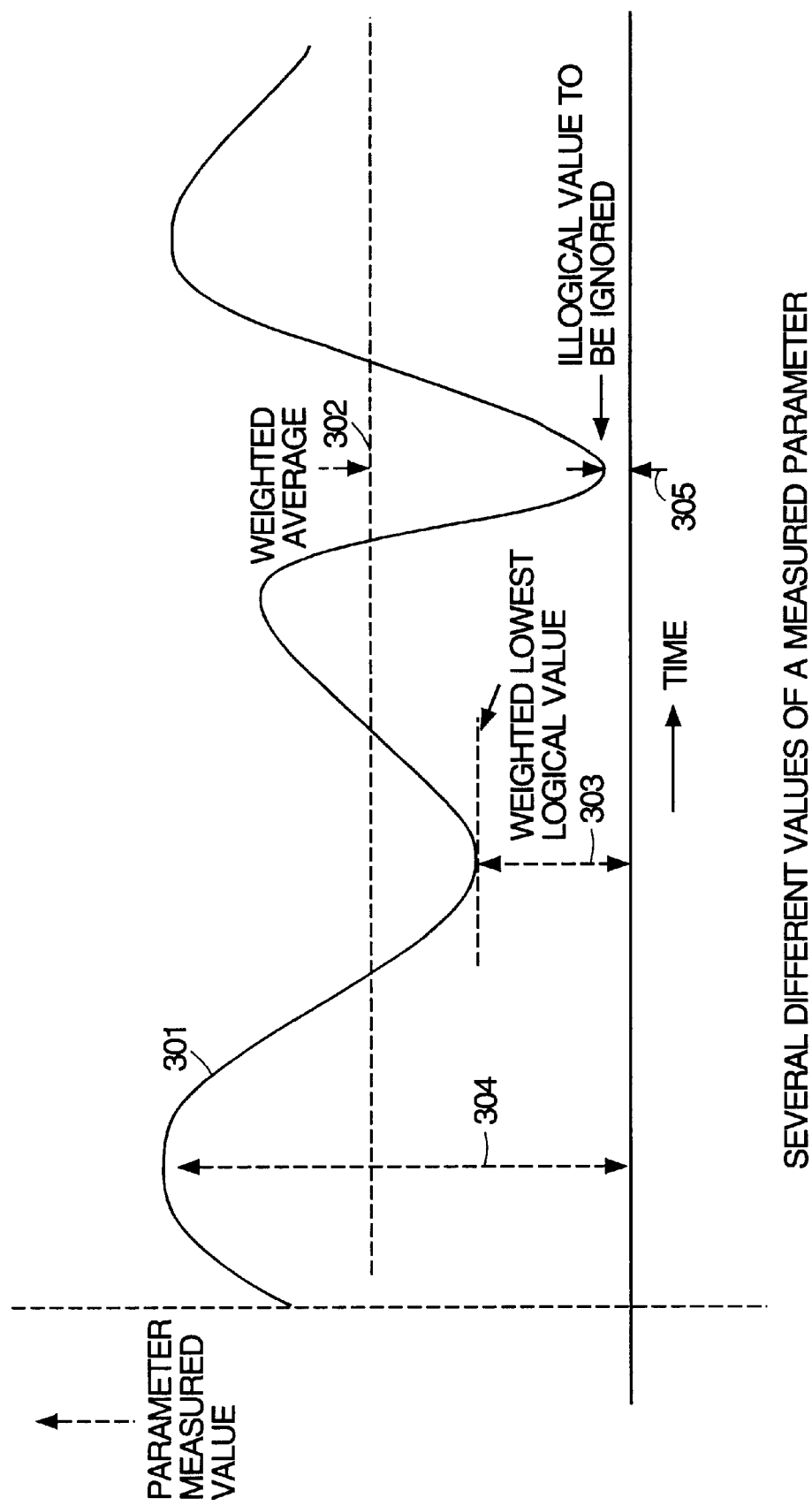
FIG. 3 illustrates how from several different changing values of a given physical condition/parameter, an optimal measured value can be selected using the program in the invention.

The program 105 advantageously chooses one of different methods of optimization such as exemplified in FIG. 3. Depending on which method of optimizing is chosen, for example, depending on whether the maximum measured parameter value in a given time span is chosen, or the minimum 303 lowest logical value or the weighted average 302 is chosen, a corresponding weighting factor for multiplication is lined up by the program 105 for multiplication. Advantageously, the program 105 is made to ignore or trap a measured value which is illogical. By user-intervention, command default and the like, program 105 is made to proceed with whatever kind of optimizing is desired. The kind of optimization so chosen will have its corresponding predetermined multiplication weighting factors based on which zone the measured physical condition values lie in.

In the preferred embodiment described herein, as stated earlier, the parameters chosen are the lowest mean blood pressure, the lowest pH, the lowest temperature, the lowest oxygenation ratio, urine output, and presence of multiple seizures.

It is conceivable that for optimal values, average values of measured predetermined parameters (physical conditions) may be used in the system and method of the invention if so chosen by the user. In such an event, weighting factors stored in the database 106 corresponding to average values of the predetermined measured physical conditions will be used. Advantageously, the weighting factors may automatically be verified as to their applicability before use in the illness severity measurement. In an extension of the preferred embodiment referenced above, three additional physical conditions (factors) are measured and considered after weighting as controlled by the software in the program 105 of FIG. 1, to assess the mortality risk of an NICU patient being monitored. The three-factor addition is termed as Perinatal Extension, or PE, which, when added to SNAP II, will provide SNAPPE II.

Described in the following passages are some considerations which governed the choice of physical conditions and their optimal selection.

The original SNAP was cumbersome and time-consuming, limiting its use predominately to research. With the example of the successful simplification of APACHE, SAPS, and PRISM, applicants have revised and simplified SNAP into SNAP-II. Applicants had to bear in mind that the spectrum of illness and causes of death and other considerations are different in neonatal patients as compared with pediatric/adult situations. Accordingly, for NICU patients, the preferred embodiment of SNAP-II described herein is a six item physiology-based severity of illness measurement that has predictive performance that equals SNAP. Consistent with "parent" physiology scores, it uses readily available vital signs and laboratory measures obtained from routine medical records. It provides an objective, reliable measure of the initial status of an NICU patient at the time of NICU admission. SNAP-II advantageously consists of six related components.

1. Item selection: The 6 items contained in SNAP-II are listed in table 1. These were carefully selected to include definable, measurable items that maximize discrimination between sick and well newborns. Applicants, after research, have retained electronically accessible items and eliminated unreliable, weak, or infrequent items.

TABLE 1

Items Included in the SNAP-II Scores
Physiological items (SNAP-II)

lowest mean blood pressure
lowest pH
lowest temperature

TABLE 1-continued

Items Included in the SNAP-II Scores
lowest pAO$_2$/FiO$_2$ ratio
urine output
multiple seizures
Perinatal extension SNAPPE-II birth weight
small for gestational age (3$^{rd}$ %)
low Apgar score
Mortality risk computed from above 2. Specific definitions: These definitions and abstracting rules are clear and simple, ensuring accurate data acquisition. Data are collected either prospectively or retrospectively from the medical charts corresponding to the first 12 hours of admission, starting at the time of the first set of vital signs on admission and extending for exactly 12 hours. The single worst value for each item is selected and recorded, ensuring consistent reliability among abstractors. If a test were not ordered, it is assumed the clinician estimated it near normal and not needed to direct care. These items and other measured items, which are near normal, receive zero points.

3. Scoring ranges of each item: A gradient in risk for each item is reflected by dividing the derangements into zones (see below). These zones are contiguous ranges and have been optimized in their power to discriminate between survivors and non-survivors survivors. For convenience, applicants have designed a data form to simplify collection.

4. Point score for each item-range combination: Points are then awarded for each item according to degree of derangement. These points are optimized to predict mortality/survival.

TABLE 2

SNAP-II ™ Score
(Preferred Embodiment)

| Parameter Points | No Points | Moderate | Severe | Extreme |
|---|---|---|---|---|
| Lowest Mean Blood Pressure | >30 0 | 20–29 19 | <20 | |
| Lowest Temperature (F.°) | >96 0 | 95–96 8 | <95 15 | |
| pAO$_2$/FiO$_2$ Ratio | >2.5 0 | 1.0–2.49 5 | 0.3–.99 16 | <.03 28 |
| Lowest Serum pH | ≧7.20 0 | 7.10–7.19 7 | <7.1 16 | |
| Seizures | None/Single 0 | | Multiple 19 | |
| Urine Output (cc/k/hr) | >0.9 0 | 0.1–0.9 5 | <0.1 18 | |

5. SNAP-II: The sum of points awarded for each item quantifies the degree of physiologic derangement and creates a unique marker for overall illness severity. This measurement is the SNAP-II illness severity measurement.

SNAP-II=sum of points awarded for the following:

(low mean BP)+(low temp)+(low oxygenation ratio)+(low pH)+ (multiple seizures)+(low urine output)

6. SNAPPE-II: SNAP-II measures illness severity, a critical component of mortality risk. However, other factors are known to make the risk even higher. Applicants tested numerous risk factors following the same process as 1–6 above, and selected three additional perinatal items (see table below), developed specific definitions and score ranges, and assigned supplemental points. The sum of SNAP-II plus the Perinatal Extension points creates the SNAPPE-II, an estimate of mortality risk.

TABLE 3

SNAPPE-II ™ Score

| Parameter Points | No Points | Moderate | Severe |
|---|---|---|---|
| Birth Weight (gm) | ≧1000 gm | 750–900 | < |
| | 0 | 10 | 17 |
| Small for Gestational Age | ≧3rd | <3rd | |
| | 0 | 8 | |
| Apgar at 5 minutes | 7–10 | | <7 |
| | 0 | | 18 |

SNAPPE-II=sum of points awarded for the following:

SNAP-II+(BW points)+(SGA points)+(low Apgar points)

7. SNAPPE-II mortality risk: The points for each item of SNAPPE-II represent the coefficients from the logistic regression equation predicting mortality. This process can be inverted by scaling the coefficients down by a factor of 0.783, subtracting the constant, and exponentiating the mathematical term. The result is a point estimate of individual mortality risk, P(death):

$$P(death)=1/(1+e^R)$$

where

R=(SNAPPE-II*0.783)−5.1656
SNAPPE-II is defined as:
  9, if moderately abnormal low mean blood pressure OR 19, if severely abnormal low mean blood pressure +
  8, if moderately abnormal low temperature OR 15, if severely abnormal low temperature +
  5, if moderately abnormal oxygenation ratio OR 16, if severely abnormal oxygenation ratio OR 28, if extremely abnormal oxygenation ratio +
  7, if moderately abnormal low pH OR 16, if severely abnormal low pH +
  19, if presence of multiple seizures +
  5, if moderately abnormal urine output OR 18, if severely abnormal urine output +
  10, if moderately low birth weight in grams +OR 17, if severely low birth weight in grams +
  8, if moderate smallness for gestational age +
  18, if severe "Apgar" at 5 minutes.

Figure 2:
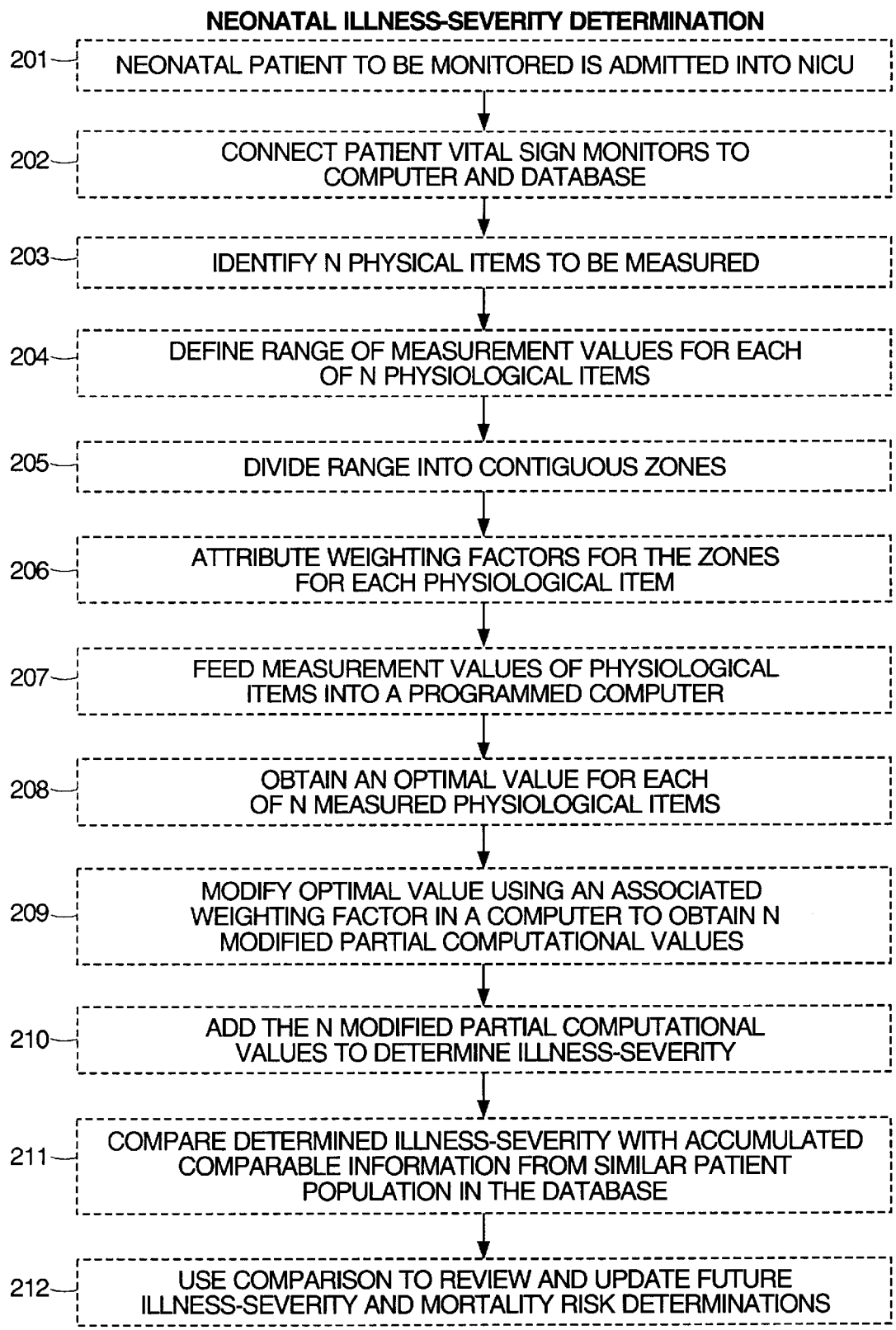
FIG. 2 illustrates the process flow of how data is acquired on a neonatal patient admitted to the NICU is monitored using the principles of the invention.

FIG. 2 is a flow diagram of an exemplary method of illness severity measurement according to the invention, and is self-explanatory. The embodiment in the FIG. 2 flow diagram is not limited to six or nine parameters. At step 201, a neonatal patient to be monitored is admitted into the neonatal intensive care unit; the patient, at step 202 is connected to the patient vital sign monitors, these in turn and to the computer and the database. At this time, arrangements are also made to obtain any manually entered physical condition readings which are entered into the patient medical records. It is within the scope of this invention to use any physical condition measurements, which can be made automatically, without any human intervention. At step 203, the n different physical items to be monitored are identified. This can be done manually, or can be done automatically by default or other methods of making a choice, e.g., by pushing a single button which is connected to make a selection of 'n', predetermined physical conditions to be measured. In block 204, all measurements of values for each chosen physical condition are extracted and fed into a buffer. Values determined to be illogical are then excluded. Then, for each parameter, the "worst" of the values is selected. Step 205 pertains to identifying the physiologic range that contains the value selected in 204. Even though in the preferred embodiment, three/four zones are indicated for practicality/simplicity, alternatively, there may be two zones or five or more zones. Step 206 pertains to attributing weighting factors for each zone of a physical condition/parameter. The software program, after taking into account several cases for similar patient population as a patient in question, decides suitable weighting factors which are used as multipliers for an optimized value of the measured physical condition. Generally, the worse the physical condition, the higher is the weighting factor. Typical weighting factors are shown in connection with a preferred embodiment in Table 2 and Table 3. In steps 207 and 208, weighted partial score for each measured parameter is chosen with the help of the software program. An example is illustrated in FIG. 3 where varying values of a measured parameter with respect to time are shown. Out of the available values, as examples, a maximum or minimum or an average or a root mean square value can be chosen by the software program. Other methods of optimizing are conceivable and within the purview of this invention. In step 209, the optimizing value is modified to generate a modified partial score for a measured parameter. In the preferred example, the modification consists in automatically identifying the applicable zone for an optimized measured parameter and finding its associated weighting factor. Other methods of modifying are within the purview of this invention. An optimized value of a parameter may, for example, be divided by a suitable weighting factor to obtain the modified partial score for the physical condition (parameter) in question. In step 210, there is an automatic addition performed of all the modified partial computational values or scores to determine illness severity. Step 211 compares the determined illness severity with other comparable information for similar patient population. The data of illness severity measurements can be used as in step 212 to review and update future illness severity and mortality risk measurements and for other suitable purposes. Some of the possible implementations of the SNAP-II system are presented in this text under the subheading "Specific applications of SNAP-II". Other uses and applications not specifically stated herein are conceivable and are intelligible to those skilled in the art.

FIG. 4 illustrates an alternative embodiment of the inventive system showing the interaction of a processor, monitoring software, and NICU patient measurement inputs.

Having collected background data and generated working modules (the coefficients for supporting the models), Applicants formed the scoring system/apparatus for hospital neonatal ICUs and physicians. As illustrated in FIG. 4, this embodiment of the present invention includes three components—(i) monitoring software, (ii) optional input accessory and (iii) system environment.

The monitoring software in the FIG. 4 embodiment is at the heart of the invention (with its beginning in SNAP-II). The software generally is executable code or a circuit or combination thereof within a digital processor/computer processor 401 (represented by dashed line box in FIG. 4). The software may include a database configured through known database techniques (i.e., programs such as Access, Paradox, and the like). A user interface enables user input of SNAP-II data items which are then stored in the database according to the database program employed. A processing member of the software is responsive to the data held in the database and calculates the SNAP-II score according to the working models of the present invention (and formulated by Applicants in the study described above). The software provides the SNAP-II score on output to the user through output means (e.g., a monitor 406, printer 409, etc.)

Optionally, various front-end, input accessories 403,404 may be employed. This includes hardware, software or combinations thereof that provide data to the database. For example, an optical scanner may be used to convert data in hard copy or paper form to electronic/digital form and store the latter in the database. If the database is coupled to a network or a general hospital system, a multiplicity of input streams may be involved. Thus, a caching subsystem and/or other clearing house subprogram may be employed to extract from the input streams pertinent SNAP-II data and store the same in the database 406.

The real utility will accrue to users 405 who harness the SNAP II (invention) measurements with the predictive equations (working models) to produce variance reports on clinical performance, resource use and inter-institutional benchmarking. There are two strategies for developing such NICU management information systems:

a. Stand alone systems. These are expansions on the scoring software described above to include equation-based benchmarks that generate regular reports for NICU managers. These systems may be quite comprehensive, and can be designed to accept data-feeds from hospital Admission/Discharge/Transfer (ADT) systems, or even hospital laboratory systems.

b. Integrated systems: In the rapidly consolidating market for electronic medical records, an alternative strategy is to partner with a major vendor of hospital electronic records. With their expertise and finding, one can work to embed the SNAP II score into the electronic chart, providing automated data acquisition and scoring, and use this to prompt actions for the clinicians in real-time. Many of the decision-support processes would depend on SNAP and related data, but also derive from the high quality, well organized care practices.

More specifically, there are several major vendors of integrated medical records systems:

i. Hewlett Packard, CareVue System: CareVue is an electronic charting system for intensive care units, including nursing flow sheets, physician notes and clinical pathways. Such a charting system is an ideal vehicle for an integrated system, because the electronic accessibility of all SNAP II components reduces data collection costs to near zero. In this setting, one can concentrate on developing the severity-adjusted variance reports and decision-support feedback in real time.

ii. Cemer: Cemer is a major vendor of hospital laboratory data management and reporting software. It has expanded into a comprehensive data repository for clinical records. The system is state-of-the-art, flexible, based on networked workstations, and using web-based technology. The Cemer system has focused its development efforts on outpatient records, so it has no specific ICU charting software similar to CareVue.

iii. Pices/Phamus: This is another major vendor of hospital comprehensive software. Others are suitable.

Substantative Differences Between the SNAP-II, CRIB, SNAP, APACHE-III, and PRISM-III This section highlights the differences among the scores that may be relevant to the present invention. In summary, CRIB and prior art SNAP are the most closely related, but are public domain scores, and the latter was invented by the applicants. APACHE-III is proprietary, but apparently applies only to adult ICU's. PRISM-III relates to children, but serves a distinctly different population in pediatric ICUs rather than NICUs, and has been developed and validated for this different purpose.

1. CRIB: CRIB was developed and validated for premature infants weighing <1500 grams at birth and/or delivered at <32 weeks gestation. It does not apply to larger or older babies and therefore cannot be used to characterize the entire population of a NICU. The score is computed from the time of birth (not admission) which makes it difficult or impossible to apply to outborn infants (infants transferred to the current hospital). Two of the physiologic items (highest and lowest "appropriate" concentration of oxygen administered) are extremely complicated to understand and to abstract and are therefore error-prone. Furthermore, these items cannot be obtained from electronic sources (i.e., laboratory computers). CRIB was validated on a cohort of infants in 1990 and has not been re-calibrated since, despite a well recognized 50 percent fall in the mortality rates (see Richardson et al. "Declining Severity Adjusted Mortality: Evidence of Improving NICU care" Pediatrics {1998; 102:893–899}). These six CRIB items blur the distinction between the mortality risk factors (birth weight, gestational age, congenital anomalies) that do not change from day to day, and degree of illness (physiologic derangements including worst base deficit, and highest and lowest "appropriate" oxygen requirement). CRIB was openly published and is now in the public domain.

2. SNAP from prior art: SNAP is a 34-item score that is cumbersome and time-consuming. SNAP-II has eliminated 28 unnecessary or redundant items. SNAP had a number of variables that are difficult and unreliable. SNAP used a 24-hour baseline data collection and scoring period. (The SNAP-II scoring period has been reduced to 12 hours to minimize "contamination" of scoring with responsiveness to treatment). SNAP weighted items based on estimates of an expert panel. (SNAP-II weights item empirically based on a logistic regression model). SNAP has supplemental points to recognize mortality risk not captured by physiologic derangement—the Perinatal Extension points of the SNAP-PE. (SNAP-II uses the same three items but these are now empirically weighted according to the logistic regression model). SNAP was openly published and is now in the public domain.

3. APACHE-III: APACHE and APACHE-II were both openly published public domain scores. APACHE-III was developed as a private venture. The scores and definitions have been released publicly. The rest has been held as trade secrets. This includes the score ranges and points, the equations relating APACHE-III to a variety of outcomes, the computer programs developed to compute and display results, and the APACHE reference database. APACHE scoring applies only to adult ICUs and is not applicable to children or particularly to newborns because of their very different physiology and diseases.

4. PRISM: The PSI and PRISM were openly published scores, and are in public domain. PRISM-III is, as aforesaid, disclosed in published European application EP 0 764 914 A2. At least some of the distinction between SNAP-II and PRISM-III which are critical to an understanding of the present invention follow:

a. Patient population: SNAP-II claims applicability to all patients in newborn intensive care units (NICUs). PRISM-III claims applicability to all patients in pediatric intensive care units (PICUs) which may include some newborns. Patient assignment to NICU or PICU may vary slightly among hospitals, but is dominated by age. PICUs serve predominantly older children and virtually no premature infants, whereas NICUs have all newborns, predominantly premature infants. Another critical difference in population between NICUs and PICUs is the range of diagnoses. PICUs serve a wide variety of conditions including infections, cancer, surgery, etc., whereas NICUs server predominantly premature infants, or term infants with disorders of fetal-neonatal transition, congenital anomalies, and birth accidents.

b. Score items: Each score has selected and optimized items to predict mortality in the respective ICU setting. The definitions and score ranges reflect the physiology of the respective age groups and technologies and practice patterns in the different types of ICUs. PRISM-III adjusts for diagnoses; and the current SNAP-II does not.

c. Scores: The scores for the different methods of illness severity measurement in prior art are the sum of the individual selected parameters and are therefore not related nor compatible with illness severity measurements from the present invention.

d. Equations: While the forms of the equations are similar (both derived from the logistic models) the coefficients and constants are different and optimized to the populations and diseases of the respective ICUs.

e. Reference databases: Applicants believe that there is nothing proprietary regarding databases for either product; both retain control through limited access and trade secret protections. In both systems, the reference database is vital for providing benchmarking of performance on several outcomes.

Advantages of the Present Invention

1. Priority in newborn scoring: Applicants believe they were the first to develop and report physiology-based illness severity scoring for newborns with SNAP. SNAP-II is derived from SNAP.

2. Unique items selection: Of the hundreds of potential predictors, applicants have selected the 6 that best capture illness severity, and include items from each organ group.

3. Unique score weights: The score weights are based on the logistic regression model used to derive the score. These weights represent optimized measures of mortality risk.

4. Unique scores for SNAP-II and SNAPPE-II: The summary scores are computer determinations from unique components to create a unique combination, reflecting multi-system physiologic arrangements and mortality risk.

5. Unique mortality risk equation. This equation was derived and validated on over 27,000 cases, ensuring a precise and robust estimate of mortality risk.

6. Unique computer program. The items, definitions, scores and computations are embodied in a first generation computer program that calculates scores and mortality risks for populations of patients in newborn intensive care.

Implementation of the SNAP-II System

SNAP-II, SNAPPE-II and SNAP-II mortality risk are intended as an integral part of a comprehensive NICU outcome evaluation and reporting system. Applicants are committing each component to a software implementation, both as stand-alone programs and embedded in larger commercial ICU charting and decision support programs. The components of applicants' system are:

1. NICU admissions and outcomes database. It is essential to record the key risk factors, treatment processes and outcomes of all NICU admissions. An example of this is the Neonatal Minimum Database System (NMDS) which contains a strictly limited set of the key risk factors, events and outcomes that permit full characterization of the performance of a given NICU.

2. SNAP-II. The collection of the 6 items, plus the Perinatal Extension risk factors permit measurement of severity of illness and mortality risk on admission.

3. Risk adjustment of outcomes. The risk-adjusted performance of a NICU can be calculated for each of several outcomes. Each risk adjustment equation is intended for inclusion in this patent application. The process of risk adjustment is carried out as follows. Individual risk factors for each patient are combined with the SNAP-II on that patient to generate an individualized risk (i.e., a probability between 0 and 1) for that specific outcome. The sum of these risks for a designated population represents be "expected" incidence of that adverse outcome. The actual or "observed" incidence for that same population is then tallied and compared to the expected rate. The ratio of the observed to the expected rate is called a standardized rate, and is used for comparisons of performance (see below). Applicants have developed risk-adjustment equations for the following:

a. Mortality. Mortality was used as the standard for developing the SNAP-II score. It is possible to calculate standardized mortality rates for any size population (see equations above).

b. Morbidity. Currently, equations are available in prior art to calculate risk of intraventricular hemorrhage (a dangerous complication of prematurity associated with brain damage), and neonatal chronic lung disease (an expensive, disabling consequence of extreme prematurity).

c. Lengthy of Stay. Illness severity has a powerful influence on length of stay for newborns. The present invention can assist to predict the length of stay and of populations of newborns which is extremely helpful in projecting workload and occupancy and comparing efficiency of clinical practice styles.

4. Report generation using simple charts and graphics is rendered possible by the system of the present invention, to compare current and past performance regarding illness severity prediction.

5. Benchmarking. Using the reference data gathered by our three research institutions, available in the database and new data which can be generated by the present invention, it is possible to compare performance of any given NICU with all others and with NICUs of similar type of patient characteristics. This benchmarking is extremely valuable to clinicians, administrators and insurers.

Specific Applications of SNAP-II

In addition to the "system" implementation described above, SNAP-II can be used independently in research, quality improvement, financial projections and medico-legal risk management.

1. Research. The variety of research applications of SNAP-II has been wide and innovative (see Richardson et al. "Neonatal Illness Severity Score: can they predict mortality and morbidity?" Clinics in Perinatology, 1998;25:591–611). Applicants are interested in making SNAP-II available to legitimate researchers to sustain those innovative applications.

2. Quality Improvement. SNAP-II can serve as an important marker for quality improvement activities. A pattern of unexpectedly ill admissions should prompt review of obstetric practices and pre-admission stabilization. A pattern of death or morbidity in patients with limited risk should prompt review of care practices and clinicians. A pattern of admission of low risk patients should prompt review of staffing and admissions policies. Many of the review processes are mandated by the Joint Commission for the accreditation of hospitals and other organizations and by many state regulations.

3. Medico-legal risk management. Several of the quality improvement screens noted above can also be sued by risk management to select cases for review to identify and reduce risks of litigation.

4. Financial projections. Current case mix adjusters are crude and retrospective. SNAP-II offers the possibility of an objective, prospective, quantitative measure of expected costs and length of stay. This can be used by hospital systems for budgeting and staffing projections, and by insurers for gauging financial exposure and for gauging financial exposure and for negotiating better reimbursement contracts.

5. Not intended for use in the ethical decision making. Applicants make no claims for the use of SNAP-II or any associated scores in estimating individual mortality risks for the purposes of withdrawing life support. All of applicants' publications have emphasized that there is insufficient certainty in estimates on any individual patient and that such decisions must be made based on clinical judgement and not based on scores.

Score for Neonatal Acute Physiology-II (SNAP-II™)

Definitions Of Physiologic Variables

Lowest Mean Blood Pressure

Lowest mean BP during the first 12 hours of admission, as recorded in the nursing flow sheet. If only systolic and diastolic are recorded, assume mean BP=diastolic+1/3 (systolic-diastolic).

Lowest Temperature

Lowest body temperature (axillary or rectal but NOT skin probe). This is usually recorded in ° F. If recorded in ° C., must convert to ° F. in order to score.

Lowest pH

Lowest pH during the first 12 hours of admission. This may be obtained by ABG, CBG or VBG, and need not be related to the @LOW, @AWP or @HIO blood gasses listed below.

Linked Respiratory Variables

The goal is to identify the three worst arterial blood gasses. These are then used to compute the $pAO_2/FiO_2$ ratio assessing oxygenation status. These three blood gasses are labeled @LOW, @AWP and @HIO and are recorded as RAW DATA.

@LOW

Low Blood gas is that with ABSOLUTE LOWEST $pAO_2$ during the TIME PERIOD. CBG, VBG, $TcPO_2$ are not acceptable alternatives. Record the following corresponding to the @LOW blood gas:

$FiO_2$@LOW: Highest $FiO_2$ expressed as percent (21%–100%).

$pAO_2$@LOW: $pAO_2$ in mm Hg.

@AWP

Lowest $pAO_2$ documented at AWP BLOOD GAS. AWP Blood gas is that with the HIGHEST MEAN AIRWAY PRESSURE. If there are several ABGs at that Mean Airway pressure, select the one with the worst $pAO_2$ unless that is already recorded as the $pAO_2$@LOW. In that case, select the next lowest. If only one blood gas was obtained, skip this step and proceed to computations. CBG, VBG, $TcPO_2$ are not acceptable alternatives. Record each of the following corresponding to the @AWP blood gas:

$FiO_2$-@AWP: Highest $FiO_2$ expressed as percent (21%–100%). Should correspond to the highest MEAN AIRWAY PRESSURE not already recorded in @LOW.

$pAO_2$@LOW: $pAO_2$ in mm Hg.

@HIO

Lowest $pAO_2$ documented at HIO BLOOD GAS. HIO Blood gas is that with the HIGHEST $FiO_2$. If there are several ABGs at that highest $FiO_2$, select the one with the worst $pAO_2$ unless that is already recorded as the @LOW or the @AWP $pAO_2$. In that case, select the next lowest. If only one blood gas was obtained, skip this step and proceed to computations. CBG, VBG, $TcPO_2$ are not acceptable alternatives. Record each of the following corresponding to the @HIO blood gas:

$FiO_2$-@HIO: Highest $FiO_2$ expressed as percent (21%–100%). Should correspond to the highest $FiO_2$ not already recorded in @LOW or @AWP.

$pAO_2$ @HIO: $pAO_2$ in mm Hg.

Lowest $pAO_2/FiO_2$ Ratio

The lowest $pAO_2/FiO_2$ ratio is computed using $pAO_2$ in torr, and $FiO_2$ as percent (e.g.: 80 torr/40% inspired oxygen= 20). Use the pairs from @LOW, @AWP or @HIO, and select whichever is lowest.

Urine Output (CC/KG/HR)

Total Cubic centimeters of urine output during the first 12 hours of admission divided by BIRTH WEIGHT IN KG, and then divided by 12 HOURS. If notes indicate that some output was lost/unmeasured, then score as 0.

Seizure

Multiple seizures, confirmed or high degree of suspicion. A single seizure or suspected seizure does not qualify.

Alternative Parameter Measurement

Blood pressure, pH, temperature and oxygenation ratio as well as Apgar ratio may be measured, tracked, and transmitted in any alternative conventional manner, either in an analog or digital fashion, as feasible in the NICU setting. Structured details of such monitors, transducers, analog/digital converters, and measuring systems are not critical to the present invention and are known to those skilled in the art.

Physical conditions such as presence of seizures and urine measurement may be done either automatically without human intervention, or manually, as conditions permit. In any event, measured values of these parameters/physical conditions also can be subjected to the step of optimizing, to choose a desirable type of measurement. In the particular embodiment described herein above, the presence of multiple seizures is a potentially significant predictor.

SNAP-II score computation may be done in real time as data items are entered in the database. Data entry for a given patient may be at one or multiple sittings, such that a current SNAP score is computed at each sitting.

Likewise, the present invention may generate real time model predictions based on computed SNAP score (as often as the score is computed). The present invention would thus be linked to reporting systems or other output means for presenting model predictions in real time to physicians, utilization review, hospital administrators, and the like. To that end, output may initially be in the form of prompts for decision (logic) making according to industry, local or health care insurance standards, or a combination thereof.

A recommended data entry format for severity of illness evaluation by using the present invention is shown in the chart below.

SNAP-II™ Severity of Illness Evaluation
Instruction
1. The most abnormal values of each physiologic parameter should be noted on this sheet.
2. The scoring period for SNAP is the first 12 hours of each patient's admission. The time of the first vital signs will be used as the time of admission.
3. Please refer to the scoring manual for details of definitions. Abstractors must adhere strictly to these definitions.

TABLE 4

|  | Highest | Lowest | SCORE |
|---|---|---|---|
| Mean Blood Pressure |  |  |  |
| Temperature |  |  |  |
| Serum pH (art/cap) |  |  |  |
| Arterial Blood Gases | FiO$_2$ percent | pO$_2$ mmHG | pO$_2$/FiO$_2$ ratio | SCORE (select worst) |
|  |  |  | SCORE |
| Multiple Seizures |  | Absent | Present |
| Total Urine Output |  | cc | cc/kg/hr |
| in first 12 hours |  |  |  |
|  | SNAP-II ™ Score |  |  |
| Birth Weight |  |  |  |
| Gestational Age |  |  |  |
| SGA (<3$^{rd}$ percentile) |  | Yes | No |
| Apgar <7 at 5 minutes |  | Yes | No |
|  | SNAPPE-II ™ Score |  |  |

EQUIVALENTS

While this invention has been particularly shown and described with reference to preferred embodiments thereof, it will be understood by those skilled in the art that various changes in form and details may be made therein without departing from the spirit and the scope of the invention as defined by the appended claims. Those skilled in the art will recognize or be able to ascertain using no more than routine experimentation, many equivalents to the specific embodiments of the invention described specifically herein. For instance, even though the monitoring of the absence/presence of seizures, and the measurement of urine output are shown in the exemplary embodiment as manual inputs, it is conceivable that urine output measurements and monitoring for seizures can be automated without any human intervention. The automated inputs from the urine output measurements and seizure monitoring can be directly fed into the user interface and/or the unit 105 comprising the software program and computer in the schematic FIG. 1. Also, instead of the preselected physical conditions of blood pressure, pH, temperature, oxygenation ratio, urine output, and presence/absence of multiple seizures, other physical conditions may be chosen for monitoring, if such choice facilitates a specific study or comparison. Likewise, in lieu of the added measurements on parameters of birth weight, smallness for gestational age, and low Apgar score, other parameters can be chosen to arrive at a specific aspect of illness severity measurement or mortality rate. All such choices of measurable physical conditions, and different possible methods of measurement including automated, manual, and hybrid measurements are within the purview of this invention. Such equivalents are intended to be encompassed in the scope of the appended claims.

What is claimed:
1. A computerized method of making an on-line determination of illness-severity of a neonatal patient in a predetermined time span, by using a software program and optimal weighted measurement values of a predetermined 'n' number of on-line parameters from the patient being monitored, said parameters relating to n measurable predetermined physical conditions, said method comprising the steps of:
   (a) obtaining, in said predetermined time span from the neonatal patient being monitored, a plurality of measured values of each of said n physical conditions and producing, using the software program, a single optimal value from said plurality of measured values for each of n measured physical conditions wherein the n physical conditions include mean blood pressure and urine output;
   (b) using said software program, obtaining from said single optimal value a modified weighted partial score, thus generating n modified weighted partial scores for n on-line parameters from the patient being monitored; and
   (c) summing the n modified weighted partial scores to provide an indication of on-line illness-severity of the neonatal patient, which on-line severity indication can be displayed and compared with other known values, said summing including, if the neonatal patient is prematurely born, at least one additional parameter defined as a function of at least one of birth weight, smallness for gestational age and Apgar.
2. The method as in claim 1, said method including the steps of:
   (d) defining a range of possible measurement values for each of said n parameters, said range including and extending from known possible minimum to known possible maximum values of measurements of each of said n parameters;
   (e) dividing, by using user-inputs, each said range into a plurality of contiguous zones;
   (f) attributing, by using user-inputs and using said program, numerical weighting factors to characterize each zone for each of said n parameters;
   (g) determining using a computer, a zone in which an optimal value of a measured physical condition from step (a) lies, and identifying its corresponding weighting factor from step (d) above, wherein the step of obtaining a modified partial score comprises:
      (h) automatically determining, using said software program, as to in which zone said single optimal value of each of said n parameters from step (a) lies, and using an associated weighting factor from step (g) to obtain a modified and weighted partial score for each measured optimal value of each of n measured parameters, thus generating n modified weighted partial scores.
3. The method as in claim 1, where n is at least six, and where said at least six on-line parameters relating to said optimal values of said measurable predetermined physical conditions comprise:
   (1) lowest mean blood pressure;
   (2) lowest serum pH;
   (3) lowest temperature;
   (4) lowest pAO$_2$/FiO$_2$ ratio, i.e., the oxygenation ratio;
   (5) urine output; and
   (6) presence of multiple seizures.

4. The method of claim 3, wherein in step (d), the defined complete range of possible measurement values for each said parameter comprises:
   (1) more than 30 for said known maximum value and less than 20 for said known minimum value for lowest mean blood pressure;
   (2) more than 96° F. for said known maximum value and less than 95° F. for said known minimum value for lowest temperature;
   (3) more than 2.5 for said known maximum and less than 0.3 for said known minimum value for oxygenation ratio;
   (4) more than or equal to 7.20 for said known maximum and less than 7.10 for said known minimum value for serum pH;
   (5) zero for said known minimum and more than one for said known maximum value for number of seizures; and
   (6) more than 0.9 for said known maximum and less than 0.1 for said known minimum value of urine output measured in cc/kg/hr.

5. The method of claim 4, wherein said numerical weighting factors recited in step (f) above comprise values:

|  | normal zone | moderate zone | severe zone | extreme zone |
|---|---|---|---|---|
| for lowest mean blood pressure: | 0 | 9 | 19 | |
| for lowest temperature: | 0 | 8 | 15 | |
| for oxygenation ratio: | 0 | 5 | 16 | 28 |
| for lowest serum pH: | 0 | 7 | 16 | |
| for seizures: | 0 | — | 19 | ; and |
| for urine output: | 0 | 5 | 18, | and wherein said | illness severity determination comprises the sum of:
   9, if moderately abnormal low mean blood pressure OR 19, if severely abnormal low mean blood pressure +
   8, if moderately abnormal low temperature OR 15, if severely abnormal low temperature +
   5, if moderately abnormal oxygenation ratio OR 16, if severely abnormal oxygenation ratio OR 28, if extremely abnormal oxygenation ratio +
   7, if moderately abnormal low pH OR 16, if severely abnormal low pH +
   19, if presence of multiple seizures +
   5, if moderately abnormal urine output OR 18, if severely abnormal urine output +.

6. The method as in claim 5 including the step of holding in memory the listed numerical weighting factor values and their corresponding parameter values for said normal, moderate, and severe zones.

7. The method as in claim 6, wherein the step (g) of determining the zone and its weighting factor for each said optimal value of an on-line measured physical condition comprises:
   comparing each said optimal value with its corresponding zonal values held in memory for normal zone, moderate zone, and severe zone to:
     identify in which zone a measured optimal value lies; and
     determine from the identified zone a corresponding weighting factor which is held in memory.

8. The method as in claim 7, wherein step (h) above includes the step of checking an applicable weighting factor for correctness using said single optimal value of each of said n parameters, and automatically obtaining a modified partial score for each said measured parameter using step (g).

9. The method as in claim 1, wherein the patient is a prematurely born infant and wherein said summing includes three additional parameters comprising birth weight, smallness for gestatinal age and Apgar, where said three additional parameters have numerical weighting factors as follows:

|  | normal zone | moderate zone | severe zone |
|---|---|---|---|
| birth weight in grams: | ≧1000 gm 0 | 750–900 10 | <750 17 |
| smallness for gestational age: 0 | ≧3$^{rd}$ 8 | <3$^{rd}$ ;and | |
| Apgar at [5 minutes]: 0 | 7–10 | 18. | <7 |

10. The method as in claim 9, including the step of obtaining a score comprised of a score from claim 1 and adding a method score from said three additional parameters by way of:
   10, if the birth weight is in moderate zone +OR 17, if birth weight is in severe zone +
   8, if measured smallness for gestational age is in moderate zone +
   18, if measured "Apgar" at 5 minutes is in severe zone, to obtain a SNAPPE-II measurement.

11. The method, as in claim 10, wherein an on-line determination is made at the time the infant is admitted into a neonatal intensive care unit, including the method steps of automatically:
   (a) making a second on-line determination of subsequent illness-severity, during a predetermined time lapse of 12 hours from admission; and
   (b) making a comparison of the illness-severity at the time of admission with the said subsequent illness-severity to generate an indication of a measure of progress of the patient.

12. The method of making an on-line determination of a patient illness-severity as in claim 10 including the step of assessing a measure of mortality risk of the patient in terms of probability of death, by using a measured patient severity illness score and a predetermined mortality risk equation.

13. The method as in claim 12 wherein:

Probability of death=$P$(death)=$1/1+e^R$, where R=(SNAPPE-II×0.783)−5.1656
and SNAPPE-II is a measurement as recited in claim 10.

14. A system for making a computerized on-line determination of an illness-severity-score of a monitored neonatal patient by using measurement values of at least six on-line parameters from the monitored patient and a software program, said parameters relating to six different measurable physical conditions from the monitored patient, said system comprising:
   (a) programmed means for defining a complete range of possible measurement values for each said parameter, said complete range including an accepted range extending from known minimum to known maximum values in medical practice for each said parameter, the parameters including one parameter relating to lowest mean blood pressure and another parameter relating to urine output;

(b) programmed means for dividing each said complete range from (a) into at least three contiguous range-zones of normal, moderate, and severe, said three range-zones when viewed collectively forming each said complete range;

(c) programmed means to attribute a numerical weighting and multiplying factor to characterize each zone for each measurable physical condition;

(d) means for taking measurements of on-line physical condition values for said at least six on-line parameters from the patient being monitored and for choosing an optimal value from said measurements;

(e) programmed means for determining from (c) above as to which range-zone each optimal value of a measured physical condition value falls within, and for obtaining a modified partial weighted score for each corresponding parameter; and (f) on-line adding means connected to receive and automatically sum modified partial weighted score values to generate an on-line indication of the illness-severity-score of the monitored patient, if the monitored patient is prematurely born, the means for taking measurements further including means to make measurement values of at least one of three more parameters relating to birth weight, smallness measure for gestational age, and Apgar, and said adding means adjusting the illness-severity score to account for at least one of birth weight, smallness for gestational age and Apgar.

15. The system as in claim 14, wherein said programmed means of element (e) includes:

a comparator means for comparing each measured parameter relating to one measurable physical condition of the patient with an applicable normal, moderate, and severe zone group, to identify which zone a measured parameter falls in, and to determine a corresponding weighting factor taken from said programmed means from element (c) above.

16. The system as in claim 15 including a second comparator for comparing the generated illness-severity-score with standard illness-severity scores stored in memory to assess the degree of illness severity.

17. The system as in claim 14, wherein the monitored patient is a prematurely born infant, and further comprising means to generate a Perinatal Extended Score (SNAPPE-II), which is the sum of the illness severity measure in step (f) of claim 1 together with the sum of:

(i) a weighting factor from step (c) above based on a birth weight zone;

(ii) a weighting factor from step (c) above based on a measured smallness for gestational age; and (iii) a weighting factor from step (c) above based on measured Apgar at 5 minutes, to generate a measure of mortality.

18. The system as in claim 17 including means to evaluate a probability of death as $$P(\text{death}) = 1/(1+e^R)$$

where (R=SNAPPE-II measure×0.783)−5.1656.

19. A method of making an on-line determination of an illness-severity of a neonatal patient being monitored by using measurement values of at least six on-line parameters from the patient in a predetermined time span, said parameters relating to six measurable predetermined physical conditions, said method comprising the steps of:

(a) obtaining, from the patient being monitored, a plurality of measurements in a predetermined time span for each said measurable physical condition and choosing, using a program, an optimal value from said plurality of measured values, thus generating six optimal values for six said predetermined physical conditions in said predetermined time span, at least one parameter relating to lowest mean blood pressure and another parameter relating to urine output;

b) defining a range of possible measurement values for each said parameter, said range including a known minimum and extending to known maximum values of said parameter measurements in medical practice;

(c) dividing each said range into at least three contiguous zones of normal, moderate, and severe;

(d) attributing, by using said program, numerical weighting factors to characterize said zones;

(e) determining a zone and its weighting factor for each said optimal value from step (a), as decided by in which zone an optimal value would fall;

(f) producing a modified partial score for an optimal value of each measured parameter, thus generating six modified partial score values; and (g) automatically summing at least six said modified partial score values for the six measured parameters to obtain an on-line illness-severity measurement which can be displayed, said summing including adjusting the on-line illness-severity measurement as a function of premature birth of the patient.

20. The method as in claim 19, where said at least six on-line parameters relating to said optimal values of said measurable predetermined physical conditions comprise:

(1) lowest mean blood pressure;

(2) lowest serum pH;

(3) lowest temperature;

(4) lowest $pAO_2/FiO_2$ ratio, i.e., the oxygenation ratio;

(5) urine output; and (6) presence of multiple seizures.

21. The method of claim 20, wherein in step (b), the defined complete range of possible measurement values for each said parameter comprises:

(1) more than 30 for said known maximum value and less than 20 for said known minimum value for lowest mean blood pressure;

(2) more than 96° F. for said known maximum value and less than 95° F. for said known minimum value for lowest temperature;

(3) more than 2.5 for said known maximum and less than 0.3 for said known minimum value for oxygenation ratio;

(4) more than or equal to 7.20 for said known maximum and less than 7.10 for said known minimum value for serum pH;

(5) zero for said known minimum and more than one for said known maximum value for number of seizures; and (6) more than 0.9 for said known maximum and less than 0.1 for said known minimum value of urine output measured in cc/kg/hr.

22. The method of claim 21, wherein said numerical weighting factors recited in step (c) above comprise values:

|  | normal zone | moderate zone | severe zone | extreme zone |
|---|---|---|---|---|
| for lowest mean blood pressure: | 0 | 9 | 19 | |
| for lowest temperature: | 0 | 8 | 15 | |
| for oxygenation ratio: | 0 | 5 | 16 | 28 |
| for lowest serum pH: | 0 | 7 | 16 | |
| for seizures: | 0 | — | 19; and | |
| for urine output: | 0 | 5 | 18. | |

23. The method as in claim 22 including the step of holding in memory the listed numerical weighting factor values and their corresponding parameter values for at least said normal, moderate, and severe zones.

24. The method as in claim 23, wherein the step (e) of determining the zone and its weighting factor for each said optimal value of an on-line measured physical condition comprises:

comparing each said optimal value with its corresponding zonal values held in memory for normal zone, moderate zone, and severe zone to:
identify in which zone a measured optimal value lies; and
determine from the identified zone a corresponding weighting factor which is held in memory.

25. The method as in claim 24, wherein step (e) of claim 19 above includes the step of automatically checking a zone of a measured optimal value of a parameter and its determined weighting factor to obtain a modified partial score for each said measured parameter, wherein further an applicable weighting factor is the modified partial score for an applicable measured optimal value of a parameter.

26. The method of making an on-line determination of an illness-severity-score of a monitored patient, as in claim 19 wherein the step of adjusting in the summing step (g) includes the step of using three additional optimized measured parameters.

27. The method as in claim 26, wherein said three additional optimized parameters comprise birth weight, smallness for gestational age and Apgar at 5 minutes, all relating to the infant, to determine a severity illness score termed SNAPPE-II.

28. The method, as in claim 27, wherein an on-line determination is made at the time the infant is admitted into a neonatal intensive care unit, including the method steps of automatically:

(a) making a second on-line determination of subsequent illness-severity, during a predetermined 12-hour time lapse from admission; and (b) making a comparison of the illness-severity at the time of admission with the said subsequent illness-severity to generate an indication of a measure of progress of the patient.

29. The method of making an on-line determination of a patient illness-severity as in claim 28 including the step of assessing a measure of mortality risk of the patient in terms of probability of death, by using a measured patient severity illness score and a predetermined mortality risk equation.

30. The method as in claim 29 wherein:

$$\text{Probability of death} = P(\text{death}) = 1/1 + e^R,$$

where $R = (\text{SNAPPE-II} \times 0.783) - 5.1656$, where SNAPPE-II is an illness severity measurement obtained from the method recited in claim 21.

* * * * *

UNITED STATES PATENT AND TRADEMARK OFFICE
CERTIFICATE OF CORRECTION

PATENT NO.    : 6,193,654 B1
DATED         : February 27, 2001
INVENTOR(S)   : Douglas K. Richardson, Gabriel J. Escobar and Shoo Lee Page 1 of 1

It is certified that error appears in the above-identified patent and that said Letters Patent is hereby corrected as shown below:

Claim 9, column 20,
Lines 12-20 should read as follows:

|  | normal zone | moderate zone | severe zone |
|---|---|---|---|
| Birth weight in grams: | ≥ 1000gm<br>0 | 750 - 900<br>10 | <750<br>17 |
| Smallness for gestational age: | ≥3rd<br>0 | <3rd<br>8 | ;and |
| Apgar at [5 minutes]: | 7-10<br>0 |  | < 7<br>18. |

Claim 30, column 24,
Line 33, change "21" to read -- 27 --.

Signed and Sealed this

Sixteenth Day of October, 2001

Attest:

NICHOLAS P. GODICI
Attesting Officer     Acting Director of the United States Patent and Trademark Office